United States Patent [19]
Hibino et al.

[11] Patent Number: 6,120,765
[45] Date of Patent: Sep. 19, 2000

[54] UROKINASE PLASMINOGEN ACTIVATOR FRAGMENTS

[75] Inventors: Toshihiko Hibino; Tadahito Takahashi; Izumi Horii, all of Charlestown; Paul F. Goetinck, Boston, all of Mass.

[73] Assignee: Shiseido Co. Ltd., Japan

[21] Appl. No.: 08/142,590

[22] Filed: Oct. 25, 1993

Related U.S. Application Data

[63] Continuation-in-part of application No. 08/042,318, Apr. 2, 1993, abandoned.

[51] Int. Cl.$^7$ .............................. A61K 38/49; C12N 9/72
[52] U.S. Cl. ................... 424/96.43; 435/215; 435/172.3; 514/12; 514/13; 514/14; 514/15; 514/16; 514/17
[58] Field of Search ......................... 424/94.63; 435/215, 435/172.3; 514/12, 13, 14, 15, 16, 17

[56] References Cited

U.S. PATENT DOCUMENTS

| | | | |
|---|---|---|---|
| 4,940,666 | 7/1990 | Boyce et al. | 435/240.2 |
| 4,999,194 | 3/1991 | Broeze et al. | 424/94.63 |
| 5,366,862 | 11/1994 | Venton et al. | 435/7.1 |

OTHER PUBLICATIONS

Appella et al., "The Receptor–binding Sequence of Urokinase", *The Journal of Biological Chemistry*, vol. 262, No. 10, pp. 4437–4440, Apr. 5, 1987.

Del Rosso et al., "Modulation of Surface–Associated Urokinase: Binding, Interiorization, Delivery to Lysosomes, and Degradation in Human Keratinocytes", *Experimental Cell Research*, vol. 193, pp. 346–355, 1991.

Fibbi et al., "Interaction of Urokinase A Chain with the Receptor of Human Keratinocytes Stimulates Release of Urokinase–like Plasminogen Activator", *Experimental Cell Research*, vol. 187, pp. 33–38, 1990.

Fraki et al., "Uninvolved Skin from Psoriatic Patients Develops Signs of Involved Psoriatic Skin After Being Grafted onto Nude Mice", *Science*, vol. 215, pp. 685–687, Feb. 5, 1982.

Grant et al., "Active and Pro–plasminogen Activator on the Surface of Human Bladder Cancer Cells Derived from a High Grade Invasive Tumor", *Biochemical and Biophysical Research Communications*, vol. 172, No. 2, pp. 870–876, Oct. 30, 1990.

Grøndahl–Hansen et al., "Urokinase–and Tissue–Type Plasminogen Activators in Keratinocytes During Wound Reepithelialization In Vivo", *Invest. Dermatol.*, vol. 90, No. 6, pp. 790–795, Jun. 1988.

Hibino et al., "Enhanced Expression of Human Pro–urokinase cDNA in *Escherichia coli*", *Agric. Biol. Chem.*, vol. 52, No. 2, pp. 329–336, 1988.

Kirchheimer et al., "Proliferation of a human epidermal tumor cell line stimulated by urokinase", *FASEB J.*, vol. 1, No. 2, pp. 125–128, 1987.

Lazarus et al., "Proteinase Metabolism in Human Skin: The Role of Plasminogene Activator and Mast Cell Proteinases in Cutaneous Biology", *Physiology, Biochemistry, and Molecular Biology of the Skin*, $2^{ed}$, Editor Goldsmith, 1991.

Meissauer et al., "Urokinase–Type and Tissue–Type Plasminogen Activators are Essential for in Vitro Invasion of Human Melanoma Cells", *Experimental Cell Research*, vol. 192, pp. 453–459, 1991.

Miganatti et al., "Tumor Invasion through the Human Amniotic Membrane Requirement for a Proteinase cascade", *Cell*, vol. 47, pp. 487–498, Nov. 21, 1986.

Nielsen et al., "A 55,000–60,000 $M_r$ Receptor Protein for Urokinase–type Plasminogen Activator", *The Journal of Biological Chemistry*, vol. 263, No. 5, pp. 2358–2363, Feb. 15, 1988.

Nykjaer et al., "Urokinase receptors in human monocytes", *Biochimica et Biophysica Acta*, vol. 1050, pp. 399–407, 1990.

Rabbani et al., "An Amino–Terminal Fragment of Urokinase Isolated from a Prostate Cancer Cell Line (PC–3) is Mitogenic for Osteoblast–like Cells", *Biochemical and Biophysical Research Communications*, vol. 173, No. 3, pp. 1058–1064, Dec. 31, 1990.

Riccio et al., "The human urokinase–plasminogen activator gene and its promoter", *Nucleic Acids Research*, vol. 13, No. 8, pp. 20–30, 1985.

Roldan et al., "Cloning and expression of the receptor for human urokinase plasminogen activator, a central molecule in cell surface, plasmin dependent proteolysis", *The EMBO Journal*, vol. 9, No. 2, pp. 467–474, 1990.

Tsubol et al., "Bimodal Relationship Between Invasion of the Amniotic Membrane and Plasminogen Activator Activity", *Int. J. Cancer*, vol. 46, pp. 56–60, 1990.

Fry et al., "Observations on Mitosis in Psoriatic Epidermis", *British Journal Dermatology*, vol. 82, pp. 19–22, 1970.

Hibino et al., "Urokinase–Plasmonogen Activator (u–PA) is Associated with Keratinocyte Proliferation", *XVII MGH Research Symposium and Poster Session*, Abstracts of Posters and Oral Presentations, Abst No. 158, Jan. 20, 1993.

Wun et al., "A Proenzyme Form of Human Urokinase", *Journal Biological Chemistry*, vol. 257, No. 12, pp. 7262–7268, 1982.

Hibino et al., "EGF–like domain of urokinase plasmogen–activator (uPA) stimulates keratinocyte growth", *The American Society for Cell Biology*, Abstract presented at the Molecular Biology of the Cell 4(Suppl.) 1993. 2/A.

Del Rosso, et al., "Role of specific membrane receptors in urokinase dependent migration of human keratinocytes", *The Journal of Investigative Dermatology*, vol. 94, No. 3, pp. 310–316, Mar. 1990.

(List continued on next page.)

*Primary Examiner*—Elizabeth Kemmerer
*Assistant Examiner*—David S. Romeo
*Attorney, Agent, or Firm*—Fish & Richardson P.C.

[57] ABSTRACT

Purified uPA peptides having, mitogenic activity and containing as few as six amino acids of the EGF-like domain of uPA.

13 Claims, 3 Drawing Sheets

OTHER PUBLICATIONS

Hibino et al., "EGF–like domain of urokinase plasmogen activator UPA plays an essential role in keratinocyte growth stimulation" *Journal of Investigative Dermatology*, 100(4):500 (1993).

Rabbani, S.A. et al. *J. Biol. Chem.* 267:14151–14156 (1992).

Au et al. Nucleotide and deduced amino acid sequences of baboon urokinase–type plasminogen activator. Nucleic Acids Res. (1990) 18:3411.

Sambrook et al. Molecular Cloning: A Laboratory Manual Second Edition vols. 1, 2 and 3. Cold Spring Harbor Laboratory Press: Cold Spring Harbor, New York, U.S.A. Nov., 1989.

Mather et al. The major fat–globule membrane proteins, bovine components 15/16 and guinea–pig GP 55, are homologous to MGF–E8 a murine glycoprotein containing epidermal growth factor–like and factor V/VIII–like sequences. Biochem. Mol. Biol. Int., (199, Mar. 1993.

SEQUENCE LISTING (1) GENERAL INFORMATION:

(iii) NUMBER OF SEQUENCES: 25

(2) INFORMATION FOR SEQ ID NO:1:

(i) SEQUENCE CHARACTERISTICS:
      (A) LENGTH: 9 amino acids
      (B) TYPE: amino acid
      (D) TOPOLOGY: linear (ii) MOLECULE TYPE: peptide (v) FRAGMENT TYPE: internal (xi) SEQUENCE DESCRIPTION: SEQ ID NO:1:

Ser Asn Lys Tyr Phe Ser Asn Ile His
1                  5

(2) INFORMATION FOR SEQ ID NO:2:

(i) SEQUENCE CHARACTERISTICS:
      (A) LENGTH: 6 amino acids
      (B) TYPE: amino acid
      (D) TOPOLOGY: linear (ii) MOLECULE TYPE: peptide (v) FRAGMENT TYPE: internal (xi) SEQUENCE DESCRIPTION: SEQ ID NO:2:

```
Ser Asn Lys Tyr Phe Ser
1               5
```

(2) INFORMATION FOR SEQ ID NO:3:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:3:

```
Asp Cys Leu Asn Gly Gly Thr Cys Val Ser Asn Lys Tyr Phe Ser Asn
1               5                   10                  15

Ile His Trp Cys Asn
            20
```

(2) INFORMATION FOR SEQ ID NO:4:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:4:

```
Asn Gly Gly Thr Cys Val Ser Asn Lys Tyr Phe Ser Asn Ile His Trp
1               5                   10                  15

Cys Asn
```

(2) INFORMATION FOR SEQ ID NO:5:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:5:

```
Thr Cys Val Ser Asn Lys Tyr Phe Ser Asn Ile His Trp Cys Asn
1               5                   10                  15
```

(2) INFORMATION FOR SEQ ID NO:6:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:6:

```
Thr Cys Val Ser Asn Lys Tyr Phe Ser Asn Ile His
1               5                   10
```

(2) INFORMATION FOR SEQ ID NO:7:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:7:

GGGGATTGCC GTGTGGAAGA                                                      20

(2) INFORMATION FOR SEQ ID NO:8:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:8:

GGAATTCGAA GGTAGCCACA GCCACGGAG                                            29

(2) INFORMATION FOR SEQ ID NO:9:

(i) SEQUENCE CHARACTERISTICS:
            (A) LENGTH: 10 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO:9:

Asp Cys Leu Asn Gly Gly Thr Cys Val Ser
1               5                   10

(2) INFORMATION FOR SEQ ID NO:10:

(i) SEQUENCE CHARACTERISTICS:
            (A) LENGTH: 9 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO:10:

Cys Leu Asn Gly Gly Thr Cys Val Ser
1               5

(2) INFORMATION FOR SEQ ID NO:11:

(i) SEQUENCE CHARACTERISTICS:
            (A) LENGTH: 8 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO:11:

Leu Asn Gly Gly Thr Cys Val Ser
1               5

(2) INFORMATION FOR SEQ ID NO:12:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:12:

```
Asn Gly Gly Thr Cys Val Ser
 1               5
```

(2) INFORMATION FOR SEQ ID NO:13:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:13:

```
Gly Gly Thr Cys Val Ser
 1               5
```

(2) INFORMATION FOR SEQ ID NO:14:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:14:

```
Gly Thr Cys Val Ser
 1               5
```

(2) INFORMATION FOR SEQ ID NO:15:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:15:

```
Thr Cys Val Ser
 1
```

(2) INFORMATION FOR SEQ ID NO:16:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (v) FRAGMENT TYPE: internal

```
        (xi) SEQUENCE DESCRIPTION: SEQ ID NO:16:

Ser Asn Ile His
1

(2) INFORMATION FOR SEQ ID NO:17:

(i) SEQUENCE CHARACTERISTICS:
         (A) LENGTH: 5 amino acids
         (B) TYPE: amino acid
         (D) TOPOLOGY: linear (ii) MOLECULE TYPE: peptide (v) FRAGMENT TYPE: internal (xi) SEQUENCE DESCRIPTION: SEQ ID NO:17:

Ser Asn Ile His Trp
1               5

(2) INFORMATION FOR SEQ ID NO:18:

(i) SEQUENCE CHARACTERISTICS:
         (A) LENGTH: 6 amino acids
         (B) TYPE: amino acid
         (D) TOPOLOGY: linear (ii) MOLECULE TYPE: peptide (v) FRAGMENT TYPE: internal (xi) SEQUENCE DESCRIPTION: SEQ ID NO:18:

Ser Asn Ile His Trp Cys
1               5

(2) INFORMATION FOR SEQ ID NO:19:

(i) SEQUENCE CHARACTERISTICS:
         (A) LENGTH: 7 amino acids
         (B) TYPE: amino acid
         (D) TOPOLOGY: linear (ii) MOLECULE TYPE: peptide (v) FRAGMENT TYPE: internal (xi) SEQUENCE DESCRIPTION: SEQ ID NO:19:

Ser Asn Ile His Trp Cys Asn
1               5

(2) INFORMATION FOR SEQ ID NO:20:

(i) SEQUENCE CHARACTERISTICS:
         (A) LENGTH: 9 amino acids
         (B) TYPE: amino acid
         (D) TOPOLOGY: linear (ii) MOLECULE TYPE: peptide (v) FRAGMENT TYPE: internal (xi) SEQUENCE DESCRIPTION: SEQ ID NO:20:

Ser Asn Ala Tyr Phe Ser Asp Ile His
1               5

(2) INFORMATION FOR SEQ ID NO:21:

(i) SEQUENCE CHARACTERISTICS:
         (A) LENGTH: 9 amino acids
```

```
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO:21:

Ser Asn Arg Tyr Phe Ser Asp Ile His
1               5

(2) INFORMATION FOR SEQ ID NO:22:

(i) SEQUENCE CHARACTERISTICS:
            (A) LENGTH: 9 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO:22:

Ser Asn Glu Tyr Phe Ser Asp Ile His
1               5

(2) INFORMATION FOR SEQ ID NO:23:

(i) SEQUENCE CHARACTERISTICS:
            (A) LENGTH: 20 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO:23:

Leu Asn Gly Gly Thr Cys Val Ser Asn Lys Tyr Phe Ser Asn Ile His
1               5                   10                  15

Trp Cys Asn Cys
            20

(2) INFORMATION FOR SEQ ID NO:24:

(i) SEQUENCE CHARACTERISTICS:
            (A) LENGTH: 18 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO:24:

Gly Gly Thr Cys Val Ser Asn Lys Tyr Phe Ser Asn Ile His Trp Cys
1               5                   10                  15

Asn Cys (2) INFORMATION FOR SEQ ID NO:25:

(i) SEQUENCE CHARACTERISTICS:
            (A) LENGTH: 157 amino acids
            (B) TYPE: amino acid
            (D) TOPOLOGY: linear (ii) MOLECULE TYPE: peptide (v) FRAGMENT TYPE: internal
```

(xi) SEQUENCE DESCRIPTION: SEQ ID NO:25:

```
Ser Asn Glu Leu His Gln Val Pro Ser Asn Cys Asp Cys Leu Asn Gly
1               5                   10                  15

Gly Thr Cys Val Ser Asn Lys Tyr Phe Ser Asn Ile His Trp Cys Asn
                20                  25                  30

Cys Pro Lys Lys Phe Gly Gly Gln His Cys Glu Ile Asp Lys Ser Lys
            35              40                  45

Thr Cys Tyr Glu Gly Asn Gly His Phe Tyr Arg Gly Lys Ala Ser Thr
        50              55                  60

Asp Thr Met Gly Arg Pro Cys Leu Pro Trp Asn Ser Ala Tyr Val Leu
65                  70              75                      80

Gln Gln Thr Tyr His Ala His Arg Ser Gln Ala Leu Gln Leu Gly Leu
                85              90                      95

Gly Lys His Asn Tyr Cys Arg Asn Pro Gln Asn Arg Arg Arg Pro Trp
            100             105             110

Cys Tyr Tyr Gln Val Gly Leu Lys Pro Leu Val Gln Glu Cys Met Val
        115             120             125

His Asp Cys Ala Asp Gly Lys Lys Pro Ser Ser Pro Pro Glu Glu Leu
    130             135             140

Lys Phe Gln Cys Gly Gln Lys Tyr Leu Arg Pro Arg Phe
145                 150             155
```

UROKINASE PLASMINOGEN ACTIVATOR FRAGMENTS

This application is a continuation-in-part of U.S. Ser. No. 08/042,318, filed on Apr. 2, 1993 now abandoned, which is hereby incorporated by reference.

BACKGROUND OF THE INVENTION

The invention relates generally to urokinase plasminogen activator and fragments thereof.

Two types of plasminogen activators, tissue type plasminogen activator (tPA) and urokinase, or urokinase plasminogen activator (uPA), are known. tPA binds directly to fibrin clots where it activates the conversion of plasminogen to plasmin. uPA is a serine protease with systemic activity. It binds to the receptor found on many cell types and converts plasminogen to plasmin on the cell surface.

SUMMARY OF THE INVENTION uPA is an approximately 55 Kd molecule which consists of (beginning at the N-terminal end) an EGF-like domain (EGF) (which corresponds to residues 1–45) a kringle domain (which corresponds to residues 46–157), and a trypsin-like protease domain (which corresponds to residues 158–411). The EGF and kringle domains make up the amino terminal fragment (AFF (SEQ ID NO:25)), which is mitogenic for human keratinocytes. uPA binds, by its EGF-like domain, to a specific membrane receptor (uPAR) expressed in many cell types. The EGF-like domain is often referred to as the growth factor domain (GFD). The amino acid residue numbering system used herein begins with residue 1 at the N terminal end of uPA.

The inventors have discovered that peptides containing as few as six amino acids of the EGF-like domain of uPA have mitogenic activity and are thought to bind to the urokinase plasminogen activator receptor (uPAR).

In general, the invention features, a uPA peptide, preferably a purified peptide, (which is capable of either or both of binding to or inducing mitogenesis in cells bearing the uPAR, e.g., epidermal cells, e.g., keratinocytes) which consists essentially of or contains more than 5 and less than 15 (or more preferably more than 5 and less than 19), contiguous amino acid residues from the growth factor domain, e.g., residues 16 through 33 (SEQ ID NO:23) (or more preferably 14 through 33), of urokinase plasminogen activator.

In preferred embodiments the peptide contains more than 5 and less than 13, (or more preferably more than 5 and less than 16), contiguous amino acid residues, inclusive, of the growth factor domain; the peptide includes the amino acid sequence Thr-Cys-Val-Ser-Asn-Lys-Tyr-Phe-Ser-Asp-Ile-His (SEQ ID NO:6); the peptide contains more than 5 and less than 10 contiguous amino acid residues, inclusive, of the domain growth factor; the peptide includes the amino acid sequence Ser-Asn-Lys-Tyr-Phe-Ser-Asp-Ile-His (SEQ ID NO:1); the peptide contains 6 contiguous amino acid residues of the domain growth factor; the peptide includes the amino acid sequence Ser-Asn-Lys-Tyr-Phe-Ser (SEQ ID NO:2).

In preferred embodiments the peptide is mitogenic for cells bearing the uPAR; the peptide binds to the uPAR but is not mitogenic for cells bearing the uPAR.

In another aspect, the invention includes a uPA peptide, preferably a purified peptide, (which is capable of either or both of binding to or inducing mitogenesis in cells bearing the uPAR, e.g., epidermal cells, e.g., keratinocytes) which consists essentially of or contains more than 5 and less than 12 contiguous amino acid residues from the amino terminal fragment, e.g., from the growth factor domain, e.g., from residues 15 through 30 of uPA.

In preferred embodiments the peptide contains more than 5 and less than 10 contiguous amino acid residues, inclusive, of the amino terminal fragment of urokinase plasminogen activator; the peptide includes the amino acid sequence Ser-Asn-Lys-Tyr-Phe-Ser-Asp-Ile-His (SEQ ID NO:1); the peptide contains 6 contiguous amino acid residues, inclusive, of the amino terminal fragment of urokinase plasminogen activator; the peptide includes the amino acid sequence Ser-Asn-Lys-Tyr-Phe-Ser (SEQ ID NO:2).

In preferred embodiments the peptide is mitogenic for cells bearing the uPAR; the peptide binds to the uPAR but is not mitogenic for cells bearing the uPAR.

In another aspect the invention includes the peptide, preferably in a purified preparation, Asn-Gly-Gly-Thr-Cys-Val-Ser-Asn-Lys-Tyr-Phe-Ser-Asn-Ile-His-Trp-Cys-Asn (SEQ ID NO:4).

In another aspect, the invention features a uPA, preferably a purified peptide, peptide in which the amino acid residue at position 23 is an amino acid other than L-lysine. In preferred embodiments: the amino acid residue at position 23 is an amino acid having a side chain with a net-positive charge at a physiological pH, e.g., at pH 7; amino acid residue at position 23 is an amino acid having a side chain which is more positively charged than is the side chain of lysine; the amino acid residue at position 23 is a basic amino acid; the amino acid residue at position 23 is any of arginine, histidine, or a positively charged or basic non-naturally occurring amino acid.

In other preferred embodiments: the amino acid residue at position 23 is an amino acid having a side chain with a net-negative charge at a physiological pH, e.g., at pH 7; the amino acid residue at position 23 is an amino acid having a side chain which is more negatively charged than is the side chain of lysine; the amino acid residue at position 23 is an acidic amino acid; the amino acid residue at position 23 is any of aspartic acid, glutamic acid, or a negatively charged or acidic non-naturally occurring amino acid.

In preferred embodiments the peptide is a full length uPA peptide.

In another aspect, the invention features a uPA peptide, preferably a purified peptide, which includes a sequence of the formula: n-$R^2$-Asn-$R^1$-Tyr-Phe-$R^3$-c, wherein, $R^1$ is an amino acid residue other than L-lysine;

$R^2$ is a sequence of between 1 and 21 residues in length, having as its carboxy-terminus $Ser^{21}$ of uPA and extending, inclusive of $Ser^{21}$, from between 1 and 21 amino acid residues in the N-terminal direction of uPA; and $R^3$ is a sequence of between 1 and 25 residues in length having as its amino-terminus $Ser^{26}$ of uPA and extending, inclusive of $Ser^{26}$, from between 1 and 25 amino acid residues in the C-terminal direction of uPA;

wherein c indicates the carboxy terminal direction of the peptide and n indicates the amino terminal direction of the peptide.

In preferred embodiments: $R^1$ is an amino acid having a side chain with a net-positive charge at a physiological pH, e.g., at pH 7; $R^1$ is a basic amino acid; $R^1$ is any of arginine, histidine, or a positively charged or basic non-naturally occurring amino acid.

In preferred embodiments: $R^2$ is any of:
n-Asp-Cys-Leu-Asn-Gly-Gly-Thr-Cys-Val-Ser-c (SEQ ID NO:9);
n-Cys-Leu-Asn-Gly-Gly-Thr-Cys-Val-Ser-c; (SEQ ID NO:10)
n-Leu-Asn-Gly-Gly-Thr-Cys-Val-Ser-c; (SEQ ID NO:11)
n-Asn-Gly-Gly-Thr-Cys-Val-Ser-c (SEQ ID NO:12);
n-Gly-Gly-Thr-Cys-Val-Ser-c (SEQ ID NO:13);
n-Gly-Thr-Cys-Val-Ser-c (SEQ ID NO:14);
n-Thr-Cys-Val-Ser-c (SEQ ID NO:15);
n-Cys-Val-Ser-c;
n-Val-Ser-c; or
n-Ser-c In preferred embodiments: $R^3$ is any of:
n-Ser-c;
n-Ser-Asn-c;
n-Ser-Asn-Ile-c;
n-Ser-Asn-Ile-His-c (SEQ ID NO:16);
n-Ser-Asn-Ile-His-Trp-c (SEQ ID NO:17);
n-Ser-Asn-Ile-His-Trp-Cys-c (SEQ ID NO:18); or
n-Ser-Asn-Ile-His-Trp-Cys-Asn-c (SEQ ID NO:19).

In preferred embodiments:
$R^2$ is n-Asp-Cys-Leu-Asn-Gly-Gly-Thr-Cys-Val-Ser-c (SEQ ID NO:9) and $R^3$ is n-Ser-Asn-Ile-His-Trp-Cys-Asn-c (SEQ ID NO:19);
$R^2$ is n-Asn-Gly-Gly-Thr-Cys-Val-Ser-c (SEQ ID NO:2); and $R^3$ is n-Ser-Asn-Ile-His-Trp-Cys-Asn-c (SEQ ID NO:19);
$R^2$ is n-Thr-Cys-Val-Ser-c (SEQ ID NO:15); and $R^3$ is n-Ser-Asn-Ile-His-Trp-Cys-Asn-c (SEQ ID NO:19);
$R^2$ is n-Thr-Cys-Val-Ser-c (SEQ ID NO:15); and $R^3$ is n-Ser-Asn-Ile-His-c; (SEQ ID NO:16)
$R^2$ is n-Ser-c and $R^3$ is n-Ser-Asn-Ile-His-c (SEQ ID NO:16); or
$R^2$ is n-Ser-c and $R^3$ is n-Ser-c; $R^1$ is Arg.

In another aspect, the invention features a uPA peptide, preferably a purified peptide, including a sequence of the formula: n-$R^2$-Asn-$R^1$-Tyr-Phe-$R^3$-c, wherein,
$R^1$ is an amino acid residue other than L-lysine;
$R^2$ is a sequence of between 1 and 21 residues in length, having as its carboxy-terminus $Ser^{21}$ of uPA and extending, inclusive of $Ser^{21}$, from between 1 and 21 amino acid residues in the N-terminal direction of uPA; and
$R^3$ is a sequence of between 1 and 25 residues in length having as its amino-terminus $Ser^{26}$ of uPA and extending, inclusive of $Ser^{26}$, from between 1 and 25 amino acid residues in the C-terminal direction of uPA;
wherein c indicates the carboxy terminal direction of the peptide and n indicates the amino terminal direction of the peptide.

In preferred embodiments: $R^1$ is an amino acid having a side chain with a net-negative charge at a physiological pH, e.g., at pH 7; $R^1$ is an amino acid having a side chain which is more negatively charged than is the side chain of lysine; $R^1$ is an acidic amino acid; $R^1$ is any of aspartic acid, glutamic acid, or a negatively charged or acidic non-naturally occurring amino acid.

In preferred embodiments: $R^2$ is any of:
n-Asp-Cys-Leu-Asn-Gly-Gly-Thr-Cys-Val-Ser-c (SEQ ID NO:9);
n-Cys-Leu-Asn-Gly-Gly-Thr-Cys-Val-Ser-c (SEQ ID NO:10);
n-Leu-Asn-Gly-Gly-Thr-Cys-Val-Ser-c (SEQ ID NO:11);
n-Asn-Gly-Gly-Thr-Cys-Val-Ser-c (SEQ ID NO:12);
n-Gly-Gly-Thr-Cys-Val-Ser-c (SEQ ID NO:13);
n-Gly-Thr-Cys-Val-Ser-c (SEQ ID NO:14);
n-Thr-Cys-Val-Ser-c (SEQ ID NO:15);
n-Cys-Val-Ser-c;
n-Val-Ser-c; or
n-Ser-c In preferred embodiments: $R^3$ is any of:
n-Ser-c;
n-Ser-Asn-c;
n-Ser-Asn-Ile-c;
n-Ser-Asn-Ile-His-c (SEQ ID NO:16);
n-Ser-Asn-Ile-His-Trp-c (SEQ ID NO:17);
n-Ser-Asn-Ile-His-Trp-Cys-c (SEQ ID NO:18); or
n-Ser-Asn-Ile-His-Trp-Cys-Asn-c (SEQ ID NO:19).

In preferred embodiments:
$R^2$ is n-Asp-Cys-Leu-Asn-Gly-Gly-Thr-Cys-Val-Ser-c (SEQ ID NO:9) and $R^3$ is n-Ser-Asn-Ile-His-Trp-Cys-Asn-c (SEQ ID NO:19);
$R^2$ is n-Asn-Gly-Gly-Thr-Cys-Val-Ser-c (SEQ ID NO:12); and $R^3$ is n-Ser-Asn-Ile-His-Trp-Cys-Asn-c (SEQ ID NO:19);
$R^2$ is n-Thr-Cys-Val-Ser- (SEQ ID NO:15)c; and $R^3$ is n-Ser-Asn-Ile-His-Trp-Cys-Asn-c (SEQ ID NO:19);
$R^2$ is n-Thr-Cys-Val-Ser-c (SEQ ID NO:15); and $R^3$ is n-Ser-Asn-Ile-His-c (SEQ ID NO:16);
$R^2$ is n-Ser-c and $R^3$ is n-Ser-Asn-Ile-His-c (SEQ ID NO:16); or
$R^2$ is n-Ser-c and $R^3$ is n-Ser-c;
$R^1$ is glutamic acid.

In another aspect, the invention features a therapeutic composition including a uPA peptide of the invention and a pharmaceutically-acceptable carrier.

In preferred embodiments: the peptide is mitogenic for cells bearing the uPAR; the peptide inhibits mitogenic activity in cells bearing the uPAR; the peptide binds to the uPAR but is not mitogenic for cells bearing the uPAR.

In another aspect, the invention features a method of regulating, e.g., promoting or inhibiting, the growth or proliferation of a cell, e.g., a cell expressing the urokinase plasminogen activator receptor, e.g., an epidermal cell, e.g., a keratinocyte, or an osteoblast. The method includes administering to the cell a growth regulating amount of a uPA peptide the invention.

In preferred embodiments: the peptide is mitogenic for cells bearing the uPAR; the peptide inhibits mitogenic activity in cells bearing the uPAR; the peptide binds to the uPAR but is not mitogenic for cells bearing the UPAR.

In preferred embodiments, the uPA peptide promotes cell growth or proliferation and the method further includes administering a growth promoting compound, other than a uPA peptide. The compound can be, e.g., a peptide growth factor, e.g., epidermal growth factor or insulin, a complex mixture or extract, e.g., pituitary extract, or a non-peptide compound, e.g., hydrocortisone.

In another aspect, the invention features, a method of regulating, e.g., promoting or inhibiting, the growth or proliferation of epidermal tissue in a patient which has been subjected to trauma, e.g., trauma arising from a disease, e.g., a disease producing an ulceration of epidermal tissue, a surgical incision, a wound, e.g., from a mechanical injury, e.g., a cut, or a burn. The method includes administering to the tissue a growth regulating amount of a uPA peptide of the invention.

In preferred embodiments: the peptide is mitogenic for cells bearing the uPAR; the peptide inhibits mitogenic activity in cells bearing the uPAR; the peptide binds to the uPAR but is not mitogenic for cells bearing the uPAR.

In preferred embodiments, the uPA peptide promotes cell growth or proliferation and the method further includes administering a growth promoting compound, other than a uPA peptide. The compound can be, e.g., a peptide growth factor, e.g., epidermal growth factor or insulin, a complex mixture or extract, e.g., pituitary extract, or a non-peptide compound, e.g., hydrocortisone.

In another aspect, the invention features a method of regulating, e.g., promoting or inhibiting, the growth of cells, e.g., a sheet of cells, e.g., a sheet of epidermal cells, e.g., keratinocytes, in vitro. The method includes culturing the cells in the presence of an effective amount of a uPA peptide of the invention.

In preferred embodiments: the peptide is mitogenic for cells bearing the uPAR; the peptide inhibits mitogenic activity in cells bearing the uPAR; the peptide binds to the uPAR but is not mitogenic for cells bearing the uPAR.

In preferred embodiments, the uPA peptide promotes cell growth or proliferation and the method further includes administering a growth promoting compound, other than a uPA peptide. The compound can be, e.g., a peptide growth factor, e.g., epidermal growth factor or insulin, a complex mixture or extract, e.g., pituitary extract, or a non-peptide compound, e.g., hydrocortisone.

In another aspect, the invention features, a method for treating an area of denuded skin in a patient, arising, e.g., from a burn, a wound, or a surgical procedure. The method includes applying cells, e.g., epidermal cells, e.g., a sheet of epidermal cells, produced according to a method of the invention to allow effective attachment of the cells to the underlying dermis of the patient. The method can include administering a uPA peptide, e.g., a growth promoting peptide of the invention, to the patient before or after the sheet is applied to the patient.

In preferred embodiments, the uPA peptide promotes cell growth or proliferation and the method further includes administering a growth promoting compound, other than a uPA peptide. The compound can be, e.g., a peptide growth factor, e.g., epidermal growth factor or insulin, a complex mixture or extract, e.g., pituitary extract, or a non-peptide compound, e.g., hydrocortisone.

In another aspect, the invention includes, a method of identifying an antagonist of uPA, e.g., of the mitogenic activity of urokinase plasminogen activator. The method includes: culturing cells, e.g., uPAR bearing cells, e.g., epidermal cells, in the presence of a uPA peptide of the invention; contacting the cells with a candidate compound; and comparing the level of mitogenic activity in the presence of the candidate compound to the level of mitogenic activity in the absence of the candidate compound, a lower level of activity in the presence of the compound being indicative that the compound is an antagonist. The candidate compound can be, e.g., an antibody, preferably a monoclonal antibody, e.g., an antibody to the uPAR, or a peptide, Mitogenic activity can be measured, e.g., by the level of [$^3$H]-thymidine incorporation.

In another aspect, the invention includes, a method of identifying an agonist of uPA, e.g., of the mitogenic activity of urokinase plasminogen activator. The method includes: culturing cells, e.g., uPAR bearing cells, e.g., epidermal cells, in the presence of a uPA peptide, e.g., a uPA peptide which inhibits mitigenic activity, contacting the cells with a candidate compound; and comparing the level of mitogenic activity, in the presence of the candidate compound to the level of mitogenic activity in the absence of the candidate compound, a higher level of activity in the presence of the compound being indicative that the compound is an agonist.

In another aspect, the invention features, a method of inhibiting the interaction of urokinase plasminogen activator with urokinase plasminogen activator receptor. The method includes contacting the receptor with a uPA peptide of the invention to inhibit the interaction.

In preferred embodiments: the peptide is mitogenic for cells bearing the uPAR; the peptide inhibits mitogenic activity in cells bearing the uPAR; the peptide binds to the uPAR but is not mitogenic for cells bearing the uPAR.

In another aspect, the invention features, a method of inhibiting the binding of urokinase plasminogen activator to a cell which expresses uPAR. The method includes contacting the cell with a uPA peptide of the invention to inhibit the interaction.

In preferred embodiments: the peptide is mitogenic for cells bearing the uPAR; the peptide inhibits mitogenic activity in cells bearing the uPAR; the peptide binds to the uPAR but is not mitogenic for cells bearing the uPAR.

In another aspect, the invention features, a method of determining the growth stage of a cell, e.g., a keratinocyte, including determining the level (e.g., by the use of an antibody or a nucleic acid probe) of urokinase plasminogen activator receptor expressed by the cell.

In another aspect, the invention features, a method for treating an animal having a disorder, e.g., a disorder characterized by an unwanted proliferation of cells, e.g., an unwanted proliferation of uPAR-bearing cells, e.g., an epidermal disorder, e.g., psoriasis, or cancer. The method includes: identifying an animal, e.g., a human, at risk for the disorder; and administering a therapeutically-effective amount of a uPA peptide of the invention to the animal.

In preferred embodiments: the peptide inhibits mitogenesis of uPAR bearing cells; the peptide is mitogenic for cells bearing the uPAR; the peptide binds to the uPAR but is not mitogenic for cells bearing the uPAR.

In preferred embodiments, the uPA peptide promotes cell growth or proliferation and the method further includes administering a growth promoting compound, other than a uPA peptide. The compound can be, e.g., a peptide growth factor, e.g., epidermal growth factor or insulin, a complex mixture or extract, e.g., pituitary extract, or a non-peptide compound, e.g., hydrocortisone.

In another aspect, the invention features, a method for mitogenically stimulating a cell bearing a uPAR, e.g., a keratinocytic cell, including contacting the cell with an effective amount of a uPA peptide of the invention e.g., a fragment of the AFF of uPA having at least six contiguous residues from the GFD.

In another aspect, the invention features, a method for inhibiting mitogenesis in a cell bearing the uPAR, e.g., a keratinocytic cell, including contacting the cell with an effective amount of a uPA peptide of the invention e.g., a fragment of the AFF of uPA having at least six contiguous residues from the GFD.

In another aspect, the invention features, a method of inhibiting the interaction of urokinase plasminogen activator with urokinase plasminogen activator receptor on a keratinocyte including contacting the receptor with an antibody to the urokinase plasminogen activator receptor to inhibit the interaction.

In another aspect, the invention features, a method for inhibiting the growth or proliferation of a cell bearing a uPAR, e.g., a dermal cell, e.g., a keratinocytic cell including contacting the cell with an antibody to the urokinase plasminogen activator receptor to inhibit growth.

In another aspect, the invention features a method of delivering a compound, e.g., a toxin molecule, e.g., a peptide toxin, to a uPAR bearing cell including providing a chimeric molecule which includes the compound coupled, e.g., by a covalent bond, e.g., by a peptide bond, to a fragment of the AFF of uPA at least six residues in length, e.g., to a uPA peptide disclosed herein.

In another aspect, the invention features, a method of inhibiting the proteolytic destruction of an extracellular protein matrix which includes cells bearing the uPAR, e.g., basement membrane, including contacting cells bearing the uPAR with a uPA peptide of the invention.

In preferred embodiments, the uPA peptide promotes cell growth or proliferation and the method further includes administering a growth promoting compound, other than a uPA peptide. The compound can be, e.g., a peptide growth factor, e.g., epidermal growth factor or insulin, a complex mixture or extract, e.g., pituitary extract, or a non-peptide compound, e.g., hydrocortisone.

In preferred embodiments: the peptide inhibits mitogenesis in uPAR bearing cells; the peptide is mitogenic for cells bearing the uPAR; the peptide binds to the uPAR but is not mitogenic for cells bearing the uPAR.

In another aspect, the invention features, a purified DNA comprising a sequence encoding a uPA peptide of the invention; a vector including a DNA sequence encoding a peptide of the invention; a cell containing the purified DNA, e.g., a cell capable of expressing peptide; an essentially homogeneous population of cells, each of which comprises the isolated DNA; a recombinantly produced peptide of the invention; and a method for manufacture of a peptide of the invention including culturing the cell in a medium to express a peptide of the invention.

The inventors have also discovered that lysine, and analogs of lysine, stimulate mitogenisis of uPAR bearing cells. Accordingly, in another aspect, the invention features a method of regulating growth of a cell, e.g., a uPAR bearing cell, e.g., a keratinocyte in vitro, or in vivo, including contacting the cell with, e.g., topically administering to the cell, a growth regulating amount of lysine, or an analog of lysine, e.g., epsilon-amino caproic acid or tranexamic acid (trans-4-(amino methyl) cyclohexane carboxylic acid.

In preferred embodiments: the lysine or analog thereof is provided at a concentration greater than is provided in growth medium used to culture said cells; lysine is provided at a concentration greater than found in fetal calf or bovine serum.

In other preferred embodiments: the cell is an animal cell, e.g., a human cell, e.g., a keratinocyte the lysine or analog thereof is contacted with the cell in situ, i.e., when the cell is part of the animal and: the concentration of lysine or an analog thereof at the surface of the cell is greater than the highest concentration that can be achieved at the surface of the cell by oral, intravenous, or other systemic administration of lysine or an analog thereof without deleterious effect on the animal; the concentration of lysine or an analog at the surface of the cell is greater than the highest concentration that is achieved at the surface of the cell when lysine or an analog thereof is administered by oral, intravenous, or other systemic administration for nutritional purposes; the lysine or analog thereof is administered to the animal at a concentration amount or dosage higher than the highest concentration, amount, or dosage that can be administered by oral, intravenous, or other systemic administration without deleterious effect on the animal; the lysine or analog thereof is administered to the animal at a concentration, amount, or dosage higher than the highest concentration, amount, or dosage that is administered by oral, intravenous, or other systemic administration of lysine or an analog thereof for nutritional purposes; sufficient lysine is administered such that the concentration of lysine in the dermis is higher, e.g., at least 20, 50, 80, 200, or 400% higher than the concentration of lysine in the dermis of a normal individual or of an individual receiving intravenous nutrition.

In another aspect, the invention features a method of regulating growth of epidermal tissue in a patient which has been subjected to trauma including administering, e.g., topically administering, e.g., to the traumatized tissue, a growth regulating amount of lysine, or an analog of lysine, e.g., epsilon-amino caproic acid or tranexamic acid (trans-4-(amino methyl) cyclohexane carboxylic acid.

In preferred embodiments: the concentration of lysine or an analog thereof at the surface of a cell in the treated tissue is greater than the highest concentration that can be achieved at the surface of a cell in the treated tissue by oral, intravenous, or other systemic administration of lysine or an analog thereof without deleterious effect on the animal; the concentration of lysine or an analog the surface of a cell in the treated tissue is greater than the highest concentration that is achieved at the surface of a cell in the treated tissue when lysine or an analog thereof is administered by oral, intravenous, or other systemic administration for nutritional purposes; the lysine or analog thereof is administered to the animal at a concentration, amount, or dosage higher than the highest concentration, amount, or dosage that can be administered by oral, intravenous, or other systemic administration without deleterious effect on the animal; the lysine or analog thereof is administered to the animal at a concentration, amount, or dosage higher than the highest concentration, amount, or dosage that is administered by oral, intravenous, or other systemic administration for nutritional purposes; sufficient lysine is administered such that the concentration of lysine in the dermis is higher, e.g., at least 20, 50, 80, 200, or 400% higher than the concentration of lysine in the dermis of a normal individual or of an individual receiving intravenous nutrition.

In another aspect, the invention features a method of regulating the growth of cells, e.g., uPAR bearing cells, e.g., epidermal cells, e.g., keratinocytes, in vitro including culturing the cells in the presence of lysine, or an analog of lysine, e.g., epsilon-amino caproic acid or tranexamic acid (trans-4-(amino methyl) cyclohexane carboxylic acid. In preferred embodiments the lysine or analog thereof is provided at a higher concentration than is lysine or an analog thereof in media used to culture, wash, or otherwise treat the cells; lysine is present in greater concentration than is found in fetal or bovine calf serum.

In another aspect, the invention features a method for treating an area of denuded skin in a patient comprising applying cells, e.g., uPAR bearing cells, e.g., epidermal cells, e.g., keratinocytes, produced according to a method described herein to allow effective attachment of the cells to the underlying dermis.

In preferred embodiments: the method further includes contacting lysine or an analog thereof with the cells after they have been applied to the patient; the concentration of lysine or an analog at the surface of the cells is greater than the highest concentration that can be achieved at the surface of the cells by oral, intravenous, or other systemic administration of lysine or an analog thereof without deleterious effect on the patient; the concentration of lysine or analog thereof at the surface of the cells is greater than the highest concentration that is achieved at the surface of the cells when lysine or an analog thereof is administered by oral, intravenous, or other systemic administration of lysine or an analog thereof for nutritional purposes; the lysine or analog thereof is administered to the patient at a concentration, amount, or dosage higher than the highest concentration amount or dosage that can be administered by oral, intravenous, or other systemic administration without deleterious effect on the patient; the lysine or analog thereof is administered to the patient at a concentration, amount, or dosage higher than the highest concentration, amount, or dosage that is administered by oral, intravenous, or other systemic administration for nutritional purposes; sufficient lysine is administered such that the concentration of lysine in the dermis is higher, e.g., at least 20, 50, 80, 200, or 400% higher than the concentration of lysine in the dermis of a normal individual or of an individual receiving intravenous nutrition.

In another aspect, the invention features, a method of promoting the growth of a cell, e.g., cell bearing a uPAR receptor, e.g., a dermal cell, e.g., a keratinocyte, which has been transferred to a site, e.g., the site of a disorder, e.g., a skin disorder or a wound, on a patient including providing the cell, applying the cell to the site, and administering to the patient, e.g., by topical application to the site, a growth promoting amount of lysine or an analog of lysine, e.g., epsilon-amino caproic acid or tranexamic acid (trans-4-(amino methyl) cyclohexane carboxylic acid.

In preferred embodiments: the lysine or analog thereof is provided at a concentration greater than is provided in growth medium used to culture said cells; lysine is provided at a concentration greater than found in fetal calf or bovine serum.

In other preferred embodiments: the concentration of lysine or an analog thereof at the surface of the cell is greater than the highest concentration that can be achieved at the surface of the cell by oral, intravenous, or other systemic administration without deleterious effect on the patient; the concentration of lysine an analog thereof at the surface of the cell is greater than the highest concentration that is achieved at the surface of the cell when lysine an analog thereof is administered by oral, intravenous, or other systemic administration for nutritional purposes; the lysine is administered to the patient at a concentration, amount, or dosage higher than the highest concentration, amount, or dosage that can be administered by oral, intravenous, or other systemic administration without deleterious effect on the patient; the lysine an analog thereof is administered to the patient at a concentration, amount, or dosage higher than the highest concentration, amount, or dosage that is administered by oral, intravenous, or other systemic administration for nutritional purposes; sufficient lysine is administered such that the concentration of lysine in the dermis is higher, e.g., at least 20, 50, 80, 200, or 400% higher than the concentration of lysine in the dermis of a normal individual or of an individual receiving intravenous nutrition.

In another aspect, the invention features a method of identifying an antagonist of the mitogenic activity of urokinase plasminogen activator including culturing uPAR bearing cells in the presence of lysine, or an analog of lysine, e.g., epsilon-amino caproic acid or tranexamic acid (trans-4-(amino methyl) cyclohexane carboxylic acid, contacting said cells with a candidate compound, and comparing the level of mitogenic activity in the presence of the candidate compound to the level of mitogenic activity in the absence of the candidate compound, a lower level of said activity in the presence of the compound being indicative that the compound is an antagonist.

In another aspect, the invention features a method identifying an agonist of urokinase plasminogen activator comprising, culturing uPAR bearing cells in the presence of lysine, or an analog of lysine, e.g., epsilon-amino caproic acid or tranexamic acid (trans-4-(amino methyl) cyclohexane carboxylic acid, contacting the cells with a candidate compound; and comparing the level of mitogenic activity, in the presence of the candidate compound to the level of mitogenic activity in the absence of the candidate compound, a higher level of activity in the presence of the compound being indicative that the compound is an agonist.

In another aspect, the invention features a method of inhibiting the interaction of urokinase plasminogen activator with urokinase plasminogen activator receptor including contacting the receptor with lysine, or an analog of lysine, e.g., epsilon-amino caproic acid or tranexamic acid (trans-4-(amino methyl) cyclohexane carboxylic acid to inhibit the interaction.

In another aspect, the invention features a method for treating an animal having a disorder including identifying an animal at risk for the disorder; and administering, e.g., topically, a therapeutically-effective amount of lysine, or an analog of lysine, e.g., epsilon-amino caproic acid or tranexamic acid (trans-4-(amino methyl) cyclohexane carboxylic acid to the animal.

In preferred embodiments: the concentration, amount, or dosage of lysine or an analog administered to the animal results in a concentration of lysine or an analog thereof at the surface of a keratinocyete of the animal that is greater than the highest concentration that can be achieved at the surface of the cell by oral, intravenous, or other systemic administration without deleterious effect on the animal; the concentration, amount, or dosage of lysine or an analog thereof administered to the animal results in a concentration of lysine or an analog thereof at the surface of a keratinocyte of the animal greater than the highest concentration that is achieved at the surface of the cell when lysine an analog thereof is administered by oral, intravenous, or other systemic administration for nutritional purposes; sufficient lysine is administered such that the concentration of lysine in the dermis is higher, e.g., at least 20, 50, 80, 200, or 400% higher than the concentration of lysine in the dermis of a normal individual or of an individual receiving intravenous nutrition.

In another aspect, the invention features a method for mitogenically stimulating a cell, e.g., a uPAR bearing cell, e.g., a keratinocytic, including contacting the cell with an effective amount of lysine, or an analog of lysine, e.g., epsilon-amino caproic acid or tranexamic acid (trans-4-(amino methyl) cyclohexane carboxylic acid.

In preferred embodiments: the lysine or analog thereof is provided at a concentration greater than is provided in growth medium used to culture said cells; lysine is provided at a concentration greater than found in fetal calf or bovine serum.

In another aspect, the invention features a method of delivering a compound to a uPAR bearing cell including providing a chimeric molecule which includes the compound coupled to lysine, or an analog of lysine, e.g., epsilon-amino caproic acid or tranexamic acid (trans-4-(amino methyl) cyclohexane carboxylic.

In another aspect, the invention features a method of inhibiting the proteolytic destruction of an extracellular protein matrix which includes cells bearing the uPAR including contacting cells bearing the uPAR with lysine, or an analog of lysine, e.g., epsilon-amino caproic acid or tranexamic acid (trans-4-(amino methyl) cyclohexane carboxylic acid.

In another aspect, the invention features therapeutic composition, e.g., a therapeutic composition suitable for topical application, including as an active ingredient lysine or an analog of lysine, e.g., epsilon-amino caproic acid or tranexamic acid (trans-4-(amino methyl) cyclohexane carboxylic acid, and a pharmaceutically-acceptable carrier. In preferred embodiments the amount of lysine or an analog in the composition is sufficient that one, two, three, five, or less than ten administrations of the composition to the patient results in: a concentration of lysine or an analog thereof at the surface of a keratinocyte of the patient that is greater than the highest concentration that can be achieved at the surface of the cell by oral, intravenous, or other systemic administration without deleterious effect on the animal; a concentration of lysine or an analog thereof at the surface of a keratinocyete of the patient greater than the highest concentration that is achieved at the surface of the cell when lysine an analog thereof is administered by oral, intravenous, or other systemic administration for nutritional purposes.

Substantially pure or purified DNA is DNA that is not immediately contiguous with both of the coding sequences with which it is immediately contiguous (i.e., one at the 5' end and one at the 3' end) in the naturally-occurring genome of the organism from which the DNA of the invention is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA or a genomic DNA fragment produced by PCR or restriction endonuclease treatment) independent of other DNA sequences. It also includes a recombinant DNA which is part of a hybrid gene encoding additional polypeptide sequence.

Homologous refers to the sequence similarity between two polypeptide molecules or between two nucleic acid molecules. When a position in both of the two compared sequences is occupied by the same base or amino acid monomeric subunit, e.g., if a position in each of two DNA molecules is occupied by adenine, then the molecules are homologous at that position. The homology between two sequences is a function of the number of matching or homologous positions shared by the two sequences. For example, 6 of 10, of the positions in two sequences are matched or homologous then the two sequences are 60% homologous. By way of example, the DNA sequences ATTGCC and TATGGC share 50% homology.

A substantially pure or purified preparation of a peptide is a preparation which is substantially free of the peptides or proteins with which the peptide (or the protein from which it is derived, e.g., whole length uPA, in the case of synthetic uPA peptides) naturally occurs in a cell.

The inventors have found that the ability to bind to uPAR and the mitogenic activity of uPA is preserved with uPA peptides as small as a 9-mer (GFD 21–29) (i.e., uPA residues 21–29 of the GFD), whose sequence is Ser-Asn-Lys-Tyr-Phe-Ser-Asn-Ile-His ((SEQ ID NO:1), and a 6-mer (GFD 21–26), whose sequence is Ser-Asn-Lys-Tyr-Phe-Ser (SEQ ID NO:2). These peptides can stimulate the growth of keratinocytes without causing side effects of tissue bleeding. The invention allows for promoting the repair of injured tissue by causing epidermal cells to be stimulated to grow and thus repair the wound.

The small size of uPA peptides of the invention, e.g., the 9-mer and the 6-mer, is important in that smaller peptides will more readily penetrate to the basal layer (the layer with mitotoic activity in the normal epidermis) and are more effective in topically stimulating epidermal cells to grow.

Peptides and methods of the invention can be used to stimulate the growth of epidermal sheets of cells in vitro or in vivo. These sheets of cells can be used, e.g., as covering for large areas of denuded skin, such as bums. The invention provides a method for stimulation of the epidermal cells, not only to produce epidermal sheets more rapidly and effectively, but also to stimulate continued growth of the epidermal cells once they are place upon the wounded tissue. The invention will enhance the ability of in vitro grown epidermal sheets applied to a patient to further grow and produce basement membrane components for effective attachment to the underlying dermis.

uPA peptides of the invention are also useful for blocking the binding of uPA to the uPAR, to thus inhibit the activity of uPA. uPA peptides having mitogenic activity, uPA peptides which bind uPAR but which do not stimulate mitogenic activity, or uPA peptides which inhibit mitogenisis, can be used. Peptides having mitogenic activity will bind and allow for cell proliferation without the proteolytic effects of uPA. The peptides not having mitogenic activity will block uPA but exhibit neither mitogenic activity nor proteolytic activity.

The inventors have also discovered that the amino acid at residue 23 of uPA plays an important role in the activity of a uPA peptide. As is described below, uPA peptides with enhanced mitogenic activity and uPA peptides with inhibitory properties can be synthesized by replacing the lysine normally found at position 23. Substituted peptides are useful for inhibiting or enhancing the growth or proliferation of cells and for receptor binding studies.

Other features and advantages of the invention will be apparent from the following description and from the claims.

DETAILED DESCRIPTION

The drawings will first be briefly described.

Drawings

Figure 1:
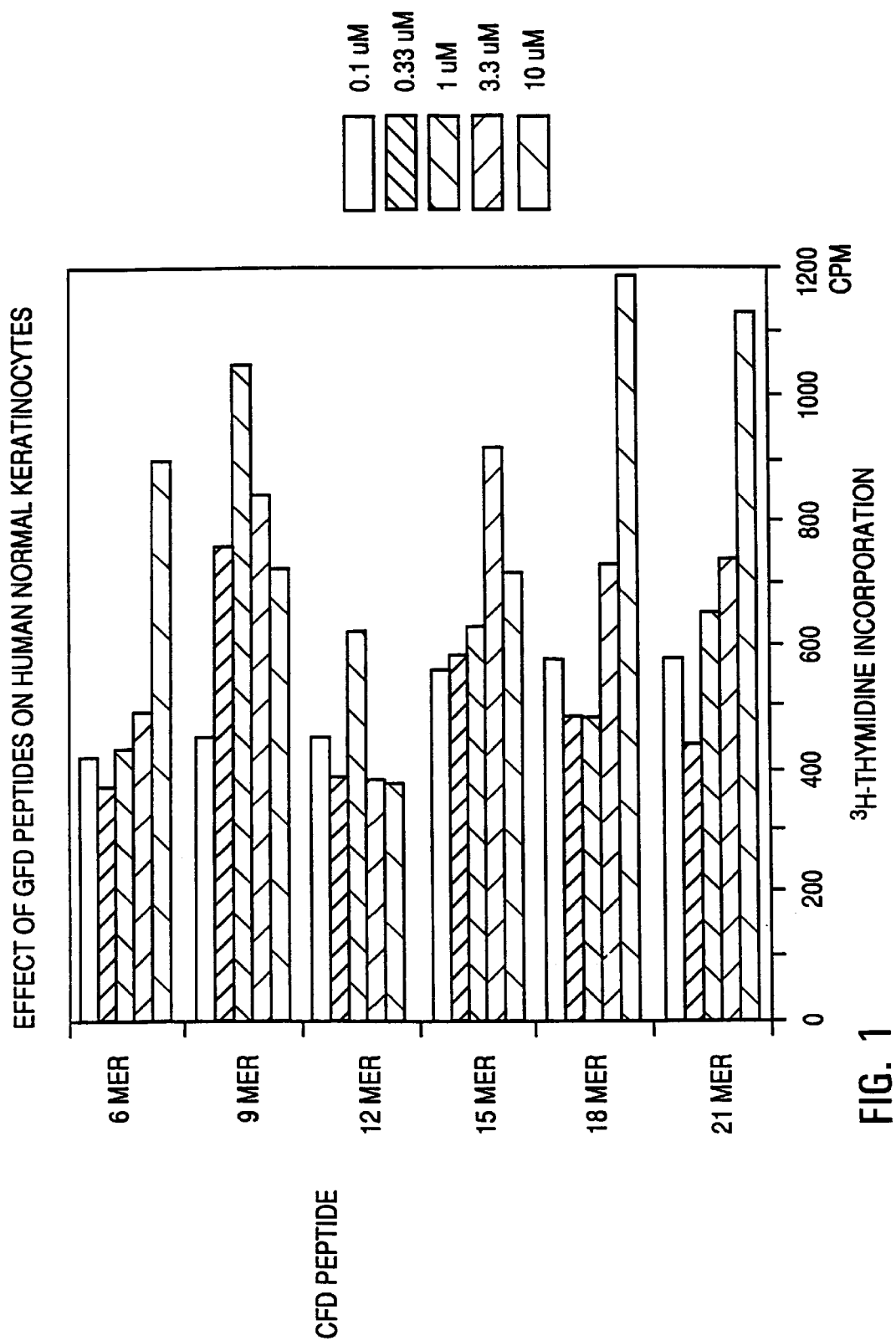

FIG. 1 is a bar graph which represents the effect of various uPA peptides on DNA synthesis in keratinocytes. Various concentrations of GFD peptides were tested in order to compare the mitogenic activity. After 24 h incubation with a peptide and 3H-thymidine, incorporated radioactivity was measured as described herein. Five concentrations were used for each peptide. For a given peptide the uppermost bar of the five represents 0.1 $\mu$M, the next lower bar 0.33 $\mu$M, the next lower bar 1 $\mu$M, the next lower bar 3.3 $\mu$M, and the lowest bar, 10 $\mu$M.

Figure 2:
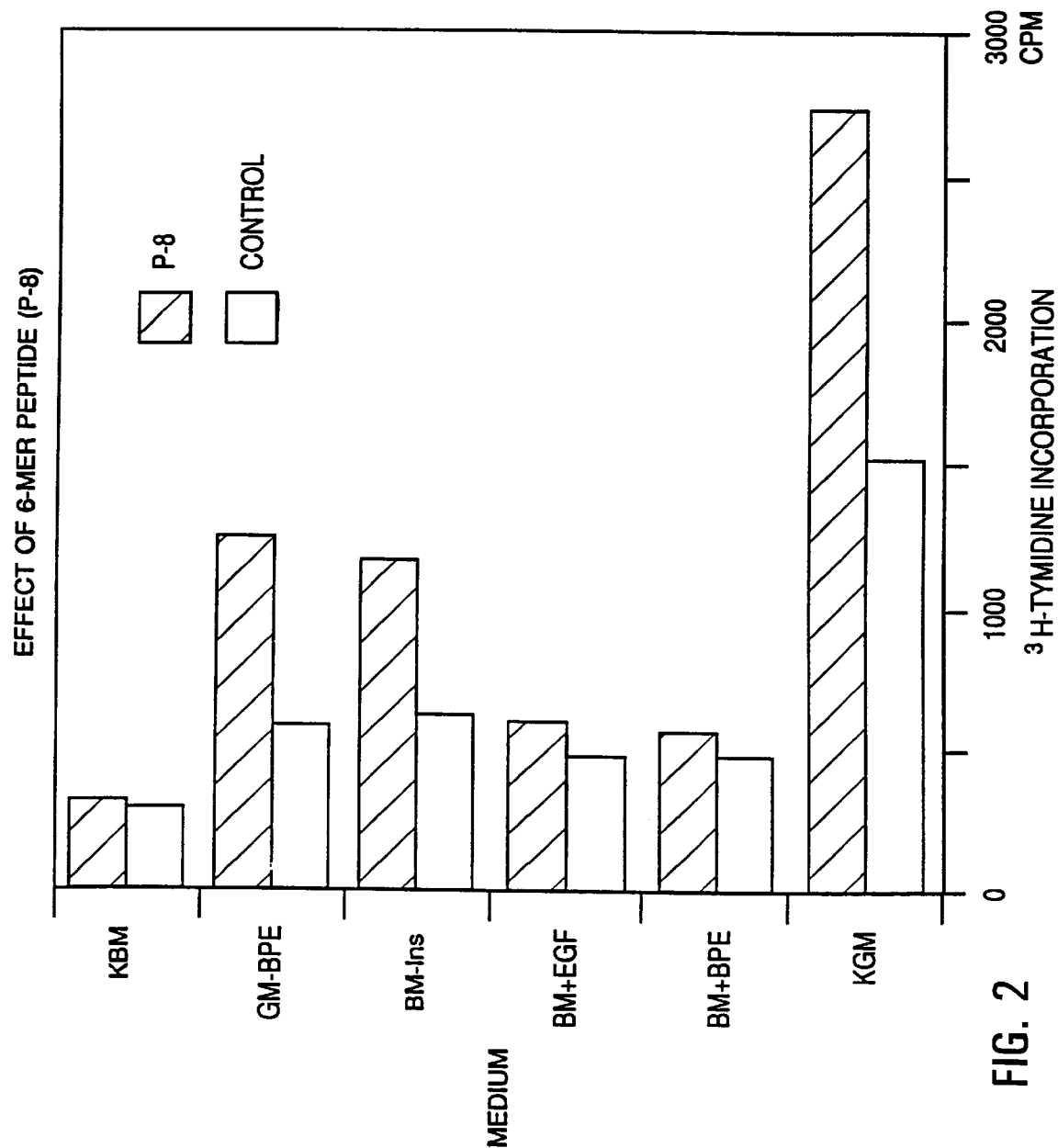

FIG. 2 is a bar graph which represents the additive effect of the 6-mer peptide in different growth media. XBM, keratinocyte basal medium (keratinocyte growth medium without epidermal growth factor, insulin, hydrocortisone, or bovine pituitary extract); KGM-BPE, keratinocyte growth medium without bovine pituitary extract; BM+Ins, keratinocyte basal medium plus insulin; BM+EGF, keratinocyte basal medium plus epidermal growth factor; BM+BPE, keratinocyte basal medium plus bovine pituitary extract; KGM, keratinocyte growth medium (Clonetics, Calif.).

Figure 3:
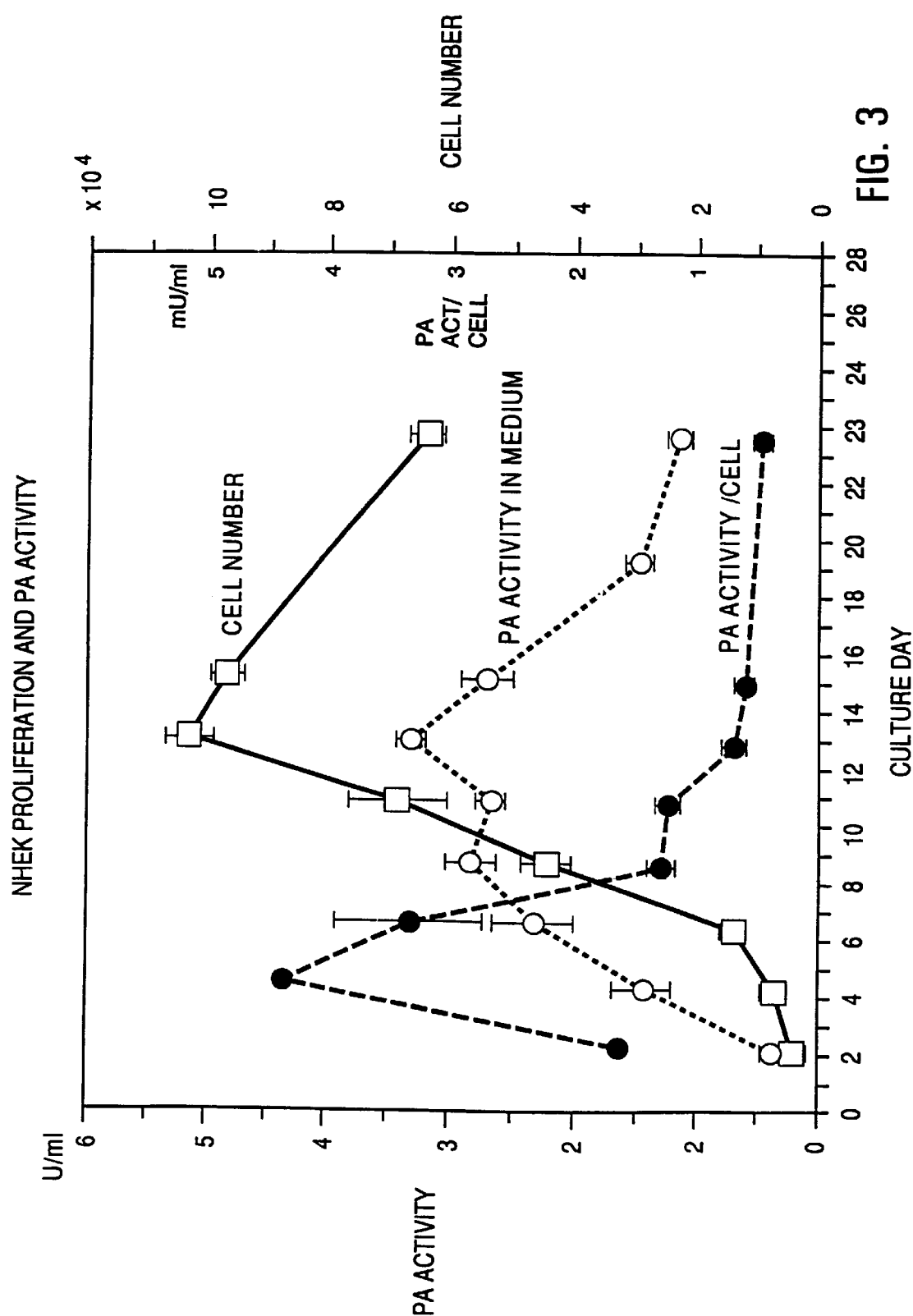

FIG. 3 is a graphic representation of uPA activity in keratinocyte culture over a 22 day period. The solid line represents total cell number; the dotted line represents total uPA activity in the medium; and the dashed line represents the uPA activity per cell.

Mitogenic Activity of uPA Fragments in Keratinocytes uPA is a 55 Kda protein which has an EGF-like domain, a kringle domain, and a trypsin-like protease domain (uPA has been cloned, see Riccio et al., 1985, *Nucleic Acids Research* 13: No. 8). uPA binds to a specific cell receptor (uPAR) through the EGF-like domain (uPAR has been cloned, see Roldan, et al., 1990 *EMBO Journal* 9:467). The 18 Kda amino terminal region of urokinase which includes the EGF-like domain and the kringle domain has been found to induce mitogenesis in an osteoblast cell line (Rablani et al., *Biochem. Biophys. Res. Commun.* 173:1058,1990).

In order to obtain small molecules which retained the mitogenic activity of uPA, but which did not have fibrinolytic activity, a number of peptides of various lengths were designed to determine the portion or portions of the uPA molecule which is required for mitogenic activity. The synthesis and analysis of these peptides is described below.

Preparation of Peptides Synthetic peptides of various lengths were synthesized according to standard methods using a peptide synthesizer (Research Genetics, Inc.). Peptides were purified by reverse phase HPLC (Toso, Inc.). The amino acid sequences are given in Table 1.

Mitogenesis Assay The effect of a peptide on mitogenesis was determined as a function of DNA synthesis as follows. Peptides (in phosphate buffered saline (PBS)) were added to the monolayers (grown as described herein) to a final concentration of either 0.1 $\mu$M, 0.33 $\mu$M, 1.0 $\mu$M, 3.3 $\mu$M, or 10 $\mu$M. 5 $\mu$L of $^3$H-thymidine (10 $\mu$Ci/ml; Amersham, Arlington Heights, Ill.) in 150 $\mu$L KGM was added to the cultures concurrent with the peptides, and cells were harvested and lysed after 24 hours at 37° C. in distilled H$_2$O using a Tomtec cell harvester, and fixed with 70% ethanol. The lysed cells were then transferred to a nylon filter (Amersham, Arlington Heights, Ill.), Beta plate scintillation fluid was added (LKB), and radioactivity was measured using a Wallac 1205 beta plate counter. Control samples, incubated in the presence of phosphate-buffered saline (PBS) and $^3$H-thymidine gave control levels of radioactivity of approximately 400 cpm.

Cell Culture Primary human keratinocytes (Clonetics, Calif.) were cultured in 96-well plates (Corning, N.Y.) in serum-free medium (KGM medium, Clonetics) to 70–80% confluency on a monolayer culture at 37° C. in 5% C02.

Short uPA Peptides Have Mitogenic Activity Several short uPA peptides were synthesized and tested for mitogenic activity as described herein. The peptides are shown in Table 1.

TABLE 1

Sequence of uPA Peptides

| | | |
|---|---|---|
| 21-mer: | DCLNGGTCVSNKYFSNIHWCN | (Seq ID No 3) |
| 18-mer: | NGGTCVSNKYFSNIHWCN | (Seq ID No 4) |
| 15-mer: | TCVSNKYFSNIHWCN | (Seq ID No 5) |
| 12-mer: | TCVSNKYFSNIH | (Seq ID No 6) |
| 9-mer: | SNKYFSNIH | (Seq ID No 1) |
| 6-mer: | SNKYFS | (Seq ID No 2) |

As shown in FIG. 1, all of the peptides tested stimulated thymidine incorporation. The 6-mer peptide did not demonstrate any measurable activity at concentrations up to 3.3 $\mu$M, but at a concentration of 10$\mu$M resulted in a significant stimulation of $^3$H-thymidine incorporation. The 9-mer peptide was effective in stimulating mitogenesis at concentrations as low as 0.33 $\mu$M, with a maximum level of mitogenic activity at 1 $\mu$M. The 12-mer demonstrated mitogenic activity only at 1 $\mu$M, and had little, if any, effect on keratinocyte stimulation at other concentrations. The highest levels of mitogenic activity produced by the 1 5-mer occurred at a concentration of 3.3 $\mu$M. At a concentration of 3.3 $\mu$M and 10 $\mu$M, the 21 -mer and the 18-mer showed similar effects on the stimulation of mitogenesis in keratinocytes. PBS controls showed approximately 400 cpm of incorporation. The entire AFF was also found to stimulate keratinocyte mitogenesis.

The Interaction of the 6-mer peptide (GFD 21–26) with Other Growth Factors

The 6-mer peptide (GFD 21–26), was studied further in order to determine its effect on keratinocyte stimulation in the presence or absence of other factors. Keratinocytes were cultured in various growth media which lacked different growth factors which are normally present in KGM (complete medium) for 24 hours in the presence or absence of the 6-mer (FIG. 2), and $^3$H-thymidine incorporation was measured as described above.

As shown in FIG. 2, the 6-mer (P-8) stimulated $^3$H-thymidine uptake greatly in the presence of the complete keratinocyte growth medium which contains various growth factors such as bovine pituitary extract (BPE), insulin, EGF, and hydrocortisone. In addition, the 6-Mer always showed additive effect to any growth factors tested in this study.

Expression of Urokinase Plasminogen Activator Receptor (uPAR) on Proliferating Keratinocytes Northern blot analysis was utilized to determine the level of uPAR expression in keratinocytes at various stages of growth. Briefly, a 0.4 kb probe which encodes the ectodomain of the uPAR was prepared by the RT-PCR technique (Invitrogen, cDNA cycle kit) using the primers: 5'-GGGGATTGCCGTGTGGAAGA-3'(SEQ ID NO:7) and 5'-GGAATTCGAAGGTAGCCACAGCCACGGAG-3' (SEQ ID NO:8). Messenger RNA was purified from cultured keratinocytes in monolayer culture at the stages of 50% confluency, 80% confluency, 100% confluency, and after confluency (120% confluency). Approximately 2 1$\mu$g of purified mRNA from each cultured keratinocyte stage was then subjected to electrophoresis in agarose and transferred to a nylon membrane (Hybond N). After pre-hybridization in 6×SSC, 5×Denhardt's, 0.5% SDS, 100 $\mu$/ml sonicated salmon sperm DNA, and 50% deionized formamide, the [$^{32}$P]-labeled uPAR probe was added, and hybridization was allowed to proceed at 42° C. overnight in the presence of 50% formamide. The nylon membrane was then washed twice with 2×SSC containing 0.1% SDS, followed by washes in 0.1×SSC, 0.1% SDS at 37° C. for 30 mins and then at 55° C. for 30 mins. Autoradiography was performed by exposing Kodak XRR film at–70° C.

The data of the Northern blot analysis indicated that uPAR mRNA is highly expressed during stages of exponential growth (e.g., at 50% confluency). In addition, the data also indicate that the expression of uPAR mRNA decreases as confluency increases over 50%, and is almost undetectable at 100% confluency. These results indicate that there is a direct correlation between the expression of the UPAR mRNA and keratinocyte proliferation.

Urokinase Plasminogen Activator Activity in Keratinocytes

Normal human keratinocytes (Clonetics, Calif.) were cultured in 96-well plates using serum free keratinocyte growth medium and cell number was monitored every two days by hemocytometer. uPA activity was also measured every two days using a two-step assay. Briefly, 50 $\mu$l of conditioned medium from the keratinocyte culture was mixed with 0.1 M Tris-HCl, pH 8.5, containing 0.1% Tween-20, and 50 $\mu$l 0.1 mg/ml purified plasminogen in PBS, and incubated for 30 mins at 30° C. Fifty microliters of 0.2 M phosphate buffer, pH 7.2, containing 1.4 M NaCl mixed with 4 mM of the substrate S-2251 (Val-Leu-Lys-p-nitroanilide; Kabi Diagnostics, Stockholm) to a final concentration of 0.8 mM S-2251, was then added. After incubation, the absorbence of each sample was measured at 405 nm, and uPA activity was determined using the International Standard of urokinase.

FIG. 3 summarizes the uPA activity in normal human epithelial keratinocytes. The unbroken line represents the cell number of keratinocytes in culture over a 22 day period, and shows that cell number rapidly increases from day 6, approaches 100% confluency at day 8, then continues to increase after 100% confluency at day 12, and begins to decline at approximately day 14. The dotted line represents the uPA activity over the same 22 day period. Total uPA production increases up to approximately day 12 and then decreases. The dashed line represents the uPA activity per cell and demonstrates that uPA activity per cell increases prior to confluence, and then decreases when confluence is reached. These data further substantiate that there is a direct correlation between uPA activity and keratinocyte proliferation.

uPA Peptides with Altered Activities

Computer analysis of the structure of uPA regions suggested the presence of a turn-structure at $Lys^{23}$ of GFD. The effect of substitutions at $Lys^{23}$ was evaluated in uPA peptides. 9mers were synthesized wherein $Lys^{23}$ was replaced by: alanine, Ser-Asn-Ala-Tyr-Phe-Ser-Asp-Ile-His (SEQ ID NO:20) (A-GFD); arginine, Ser-Asn-Arg-Tyr-Phe-Ser-Asp-Ile-His (SEQ ID NO:21) (R-GFD); and glutamic acid, Ser-Asn-Glu-Tyr-Phe-Ser-Asp-Ile-His (SEQ ID NO:22) (E-GFD).

The ability of these substituted peptides to stimulate mitogenesis was determined by $^3$H-thymidine uptake. As expected the positive control 9-mer Ser-Asn-Lys-Tyr-Phe-Ser-Asp-Ile-His (SEQ ID NO:1) (K-GFD) increased uptake as compared with untreated cells. $^3$H-thymidine uptake in cells treated with A-GFD was little different from negative control cells (no peptide). R-GFD greatly increased $^3$H-thymidine uptake, as compared with K-GFD-treated positive control cells. E-GFD on the other hand inhibited mitogenesis, $^3$H-thymidine uptake was less than that seen in negative contact cells (no peptide added). These results reveal that the amino acid residue at position 23 plays an important role in keratinocyte stimulation. Furthermore, the activity is dependent on charge as the move to a more basic residue enhanced mitogenic activity whereas substitution with negatively charged Glu resulted in an inhibitory effect. Other useful peptides can be found by synthesizing uPA peptides, e.g., peptides shown in Table 1 with various substitutions at position 23 (or other positions) and determining their effect on mitogenesis.

Use

The formulations of this invention are especially useful for topical administration, but may also be administered in other modes, e.g., parenterally, intravenously, subcutaneously, or intramuscularly. Therapeutically effective amounts (e.g., amounts which eliminate or reduce the patient's pathological condition) of the peptides of the invention can be administered to humans or other mammals to treat or inhibit conditions or disorders wherein inhibition or stimulation of cell growth is desired, e.g., in disorders wherein the promotion of keratinocyte growth is desirable.

The compounds provided herein can be formulated into pharmaceutical compositions by admixture with any pharmaceutically acceptable nontoxic excipients and carriers. As noted above, such compositions may be prepared for parenteral administration, particularly in the form of liquid solutions or suspensions; for oral administration, particularly in the form of tablets or capsules; or topically in the form of ointments, creams or gels. The compositions may conveniently be administered in unit dosage form and may be prepared by any of the methods well known in the pharmaceutical art. Formulations for parenteral administration may contain as common excipients, sterile water or saline, polyalkylene glycols such as polyethylene glycol, oils of vegetable origin, hydrogenated naphthalenes and the like. In particular, biocompatible, biodegradable lactide polymer, lactide/glycoside copolymer, or polyoxyethylene-polyoxypropylene copolymers may be useful excipients to control the release of the peptides. Other potentially useful parenteral delivery systems for these peptides include ethylene-vinyl acetate copolymer particles, osmotic pumps, implantable infusion systems, and liposomes. Formulations for parenteral administrations may also include glycocholate for buccal administration, methoxysalicylate for rectal administration, or citric acid for vaginal administration.

The materials of this invention can be employed as the sole active agent in a pharmaceutical composition or can be used in combination with other active ingredients, e.g., other compounds which facilitate cell growth or inhibition, or peptidase or protease inhibitors.

The dosage of the compounds described herein in a therapeutic composition will vary depending upon a number of factors, including the route of administration, type and state of the disease, and the overall health status of the particular patient.

The peptides of the invention can also be used in vitro, e.g., to stimulate the growth of cultured epidermal cells.

Other Embodiments

The invention includes any peptide which is substantially homologous to a uPA peptide described herein and which has biological activity. By "biologically active" is meant the ability to bind specifically to a uPAR bearing cell, e.g., a keratinocyte, or the ability to promote or inhibit the growth (mitogenesis) of a uPAR bearing cell, e.g., a keratinocyte, as determined by the assays described herein or by other assays know to those in the art. Most preferably substantially homologous peptides, fragments or analogs will have: 10%, preferably 40%, more preferably at least 90, 95, or 99%, of the activity of the 9-mer of Table 1 in the case of growth promoting peptides; and 10%, preferably 40%, more preferably at least 90, 95, or 99%, of the inhibitory activity of E-GFD, in the case of inhibitory peptides. Peptides which bind but have no effect on mitogenesis have biological activity if they bind at least 10, preferably 40, or more preferably at least 90, 95, or 99%, as well as the peptide of SEQ ID NO:1. The invention also includes chimeric peptides that include uPA peptides described herein.

The invention also includes any biologically active fragment or analog of the uPA peptides described herein. Preferred analogs include peptides whose sequences differ from the wild-type sequence (i.e., the sequence of the homologous portion of naturally occurring uPA) only by conservative amino acid substitutions, preferably by only one, two, or three, substitutions, for example, substitution of one amino acid for another with similar characteristics (e.g., valine for glycine, arginine for lysine, etc.) or by one or more non-conservative amino acid substitutions, deletions, or insertions which do not abolish the polypeptide's biological activity. Table 2 lists a number of conservative amino acid substitutions.

TABLE 2

CONSERVATIVE AMINO ACID REPLACEMENTS

| For Amino Acid | Code | Replace With |
|---|---|---|
| Alanine | A | D-Ala, Gly, Aib, β-Ala, Acp, L-Cys, D-Cys |
| Arginine | R | D-Arg, Lys, D-Lys, homo-Arg, D-homo-Arg Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, Aib, β-Ala, Acp |
| Isoleucine | I | D-Ile, Val, D-Val, AdaA, AdaG, Leu, D-Leu, Met, D-Met |
| Leucine | L | D-Leu, Val, D-Val, AdaA , AdaG, Leu, D-Leu, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, AdaA, AdaG, cis-3,4, or 5-phenylproline, Bpa, D-Bpa |
| Proline | P | D-Pro, L-I-thioazolidine-4-carboxylic acid, D-or L-1-oxazolidine-4-carboxylic acid (Kauer, U.S. Pat. No. 4,511,390) |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met, AdaA, AdaG |

Other useful modifications include those which increase peptide stability; such analogs may contain, for example, one or more non-peptide bonds (which replace the peptide bonds) or D-amino acids in the peptide sequence.

Analogs can differ from naturally occurring uPA sequence in amino acid sequence or can be modified in ways that do not involve sequence, or both. Analogs of the invention will generally exhibit at least 40%, more preferably 50%, more preferably 60%, more preferably 70%, more preferably 80%, more preferably 90%, and most preferably 95% or even 99%, homology with a naturally occurring uPA sequence or with a uPA sequence described herein.

Non-sequence modifications include in vivo or in vitro chemical derivatization of peptides, e.g., acetylation, methylation, phosphorylation, carboxylation, or glycosylation. Also included are analogs that include residues other than naturally occurring L-amino acids, e.g., D-amino acids or non-naturally occurring or synthetic amino acids, e.g., β or γ amino acids. Alternatively, increased stability may be conferred by cyclizing the peptide molecule.

Analogs, e.g., peptides differing by 1,2,3, or more residues from the peptides disclosed herein, can be prepared by methods known to those in the art and tested for biological activity by methods known in the art or disclosed herein.

Other embodiments are within the following claims.

What is claimed is:

1. A purified peptide containing more than 5 and less than 13 contiguous amino acid residues from the 18 kilodalton amino terminal region of urokinase plasminogen activator, wherein said amino acid residues include the amino acid sequence Ser-Asn-Lys-Tyr-Phe-Ser (SEQ ID NO: 2).

2. The purified peptide of claim 1, including the amino acid sequence Thr-Cys-Val-Ser-Asn-Lys-Tyr-Phe-Ser-Asp-Ile-His (SEQ ID NO: 6).

3. The purified peptide of claim 1 wherein said peptide contains more than 5 and less than 10 contiguous amino acid residues.

4. The purified peptide of claim 3, wherein said contiguous amino acid residues include the amino sequence Ser-Asn-Lys-Tyr-Phe-Ser-Asn-Ile-His (SEQ ID NO: 1).

5. The purified peptic of claim 1, wherein said peptide contains 6 contiguous amino acid residues of said 18 kilodalton amino terminal region.

6. A therapeutic composition comprising as an active ingredient a peptide of claim 1 and a pharmaceutically-acceptable carrier.

7. A peptide produced by expression of isolated DNA comprising a sequence encoding a peptide of claim 1, which is less than 13 amino acid residues in length.

8. The purified peptic of claim 1, wherein the purified peptide is Ser-Asn-Lys-Tyr-Phe-Ser (SEQ ID NO: 2).

9. The purified peptide of claim 1, wherein the purified peptide is Thr-Cys-Val-Ser-Asn-Lys-Tyr-Phe-Ser-Asp-Ile-His (SEQ ID NO: 6).

10. The purified-peptide of claim 1, wherein the purified peptide is Ser-Asn-Lys-Tyr-Phe-Ser-Asn-lle-His (SEQ ID NO: 1).

11. The purified peptide of claim 1, containing more than 5 and less than 12 contiguous amino acid residues from the 18 kilodalton amino terminal region of urokinase plasminogen activator.

12. The purified peptide of claim 1, wherein said peptide contains more than 5 and less than 10 contiguous amino acid residues, inclusive of said 18 kilodalton amino terminal region of urokinase plasminogen activator.

13. A purified peptide consisting of the amino acid sequence Asn-Gly-Gly-Thr-Cys-Val-Ser-Asn-Lys-Tyr-Phe-Ser-Asp-Ile-His-Trp-Cys-Asn (SEQ ID NO:4).

* * * * *

UNITED STATES PATENT AND TRADEMARK OFFICE
CERTIFICATE OF CORRECTION

PATENT NO. : 6,120,765
DATED : SEPTEMBER 19, 2000
INVENTOR(S) : TOSHIHIKO HIBINO ET AL.

It is certified that error appears in the above-identified patent and that said Letters Patent is hereby corrected as shown below:

Under Claims, Column 30, Claim 8, Line 1, Delete "peptic" and Insert - - peptide- -

Signed and Sealed this

Fifteenth Day of May, 2001

Attest:

NICHOLAS P. GODICI

Attesting Officer        Acting Director of the United States Patent and Trademark Office

UNITED STATES PATENT AND TRADEMARK OFFICE
CERTIFICATE OF CORRECTION

PATENT NO. : 6,120,765
DATED : September 19, 2000
INVENTOR(S) : Hibino et al.

It is certified that error appears in the above-identified patent and that said Letters Patent is hereby corrected as shown below:

Title page,
Item [73] Assignee should read as follows:

-- [73] Assignee: The General Hospital Corporation, Boston, MA --.

Signed and Sealed this

Thirtieth Day of July, 2002

Attest:

JAMES E. ROGAN
Attesting Officer          Director of the United States Patent and Trademark Office